United States Patent [19]

Peake et al.

[11] Patent Number: 5,565,451
[45] Date of Patent: Oct. 15, 1996

[54] 1-SUBSTITUTED-2, 4-DIAMINO-6, 6-DIALKYL-1, 6-DIHYDRO-1, 3, 5-TRIAZINES AS INSECTICIDES

[75] Inventors: Clinton J. Peake, Trenton, N.J.; Sarah Y. Lin, Sacramento, Calif.

[73] Assignee: FMC Corporation, Philadelphia, Pa.

[21] Appl. No.: 306,744

[22] Filed: Sep. 15, 1994

[51] Int. Cl.$^6$ .................................................. A01N 43/66
[52] U.S. Cl. ........................................................... 514/245
[58] Field of Search ............................................. 514/245

[56] References Cited

U.S. PATENT DOCUMENTS

| | | | |
|---|---|---|---|
| 2,823,161 | 2/1958 | Lux et al. | 514/245 |
| 2,836,539 | 5/1958 | Cutler | 514/245 |
| 2,897,116 | 7/1959 | Hitchings et al. | 514/245 |
| 3,123,527 | 3/1966 | Fisher | 514/245 |
| 3,155,486 | 11/1966 | Stevenson et al. | 71/2.5 |
| 3,455,895 | 7/1969 | Niilo-Rama et al. | 514/245 |

OTHER PUBLICATIONS

R. L. Blakley, "The Biochemistry of Folic Acid and Related Derivatives", pp. 464–468 (1969); Wiley and Sons, N.Y.
J. M. Blaney, et al., "Structure–Activity Relationships of Dihyrofolate Reductase Inhibitors", Chemical Reviews, vol. 84, No. 4, pp. 334–407 (1984).
E. A. Coats, et al., "Comparative QSAR of Antibacterial Dihydrofolate Reductase Inhibitors", QSAR in Design of Bioactive Compound. 84, pp. 71–85 (1985).
E. J. Modest, et al., "Chemical and Biological Studies on 1,2–Dihydro–s–Triazines", JOC, 21 pp. 14–20 (1956).

*Primary Examiner*—Allen J. Robinson
*Attorney, Agent, or Firm*—Stanford M. Back; Robert M. Kennedy

[57] ABSTRACT

An insecticidal composition comprising, in admixture with an agriculturally acceptable carrier, an insecticidally effective amount of a 1,3,5-triazine compound of the formula

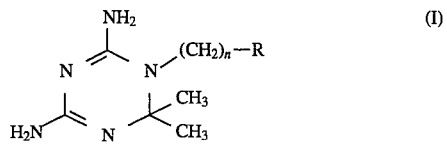

(I)

where n is 0–4; and R is lower alkyl, or

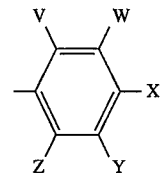

wherein V, W, X, Y, and Z are as defined herein; and methods of using this composition.

7 Claims, No Drawings

1-SUBSTITUTED-2, 4-DIAMINO-6, 6-DIALKYL-1, 6-DIHYDRO-1, 3, 5-TRIAZINES AS INSECTICIDES

BACKGROUND OF THE INVENTION

This invention relates to substituted 1,3,5-triazine compounds and compositions containing the same (hereinafter "substituted triazines") which are useful for controlling insects in agricultural crops. More particularly, this invention relates to certain 1-substituted 2,4-diamino-6,6-dialkyl-1,6-dihydro-1,3,5-triazine compounds and compositions, and their use as insecticides against a variety of insects, including larvae such as the tobacco budworm.

SUMMARY OF THE INVENTION

In accordance with the present invention it has been found that certain substituted triazines, as defined hereinbelow, and agriculturally acceptable salts thereof, when present in insecticidally effective amounts and with a suitable agricultural carrier, are useful as active ingredients in the insecticidal compositions and methods of this invention. These substituted triazines may be represented by the following generic structure:

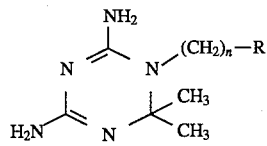

where n is 0–4; and R is lower alkyl [e.g., —CH(CH$_3$)$_2$], or

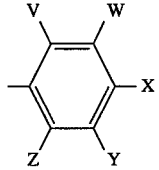

wherein

Z is hydrogen;

V, W, X, and Y are independently selected from hydrogen, halogen (e.g., chlorine, fluorine), straight or branched chain lower alkyl, (e.g., CH$_3$, —C$_2$H$_5$, n-C$_3$H$_7$, —CH(CH$_3$)$_2$, n-C$_4$H$_9$, —CH(CH$_3$)(C$_2$H$_5$)), lower haloalkyl (e.g., —CF$_3$), lower alkoxy (e.g., —OCH$_3$, n-OC$_4$H$_9$, n-OC$_5$H$_{11}$), lower alkylthio (e.g., —SCH$_3$), dialkylamino (e.g.,—N(CH$_3$)$_2$), dialkylaminoalkyl (e.g., —CH$_2$N(C$_2$H$_5$)$_2$), cyano, nitro, cycloalkylalkyl (e.g., 5-cyclohexylpentyl), bicycloalkoxy (e.g., decahydronaphth-2-yloxy), optionally substituted arylalkyl (e.g., phenylmethyl, 2-phenylethyl, 1-phenylpropyl, 4-(2-chloro-4-fluorosulfonylphenyl)butyl), optionally substituted arylalkoxy [e.g., phenylmethoxy, 2-chlorophenylmethoxy, 4-chlorophenylmethoxy], aryloxyalkyl (e.g., naphth-2-yloxymethyl), heteroarylalkyl (e.g., pyridin-4-ylmethyl), lower alkylcarbonyl (e.g., methylcarbonyl), lower alkoxycarbonyl (e.g., ethoxycarbonyl), arylcarbonyl (e.g., phenylcarbonyl), and substituted arylaminocarbonylalkyl [e.g., 2-[(4-fluorosulfonylphenyl)aminocarbonyl]ethyl]; or V and W, taken together, are —OC(CH$_3$)$_2$CH$_2$—, to form a 2,3-dihydro-2,2-dimethylbenzofuran-7-yl ring system; and agriculturally acceptable salts thereof.

Agriculturally acceptable salts of the 1,3,5-triazines include, but are not limited to, for example, the salts of hydrochloric acid, ethanesulfonic acid, gluconic acid, and pamoic acid.

Of the compounds of the present invention, the more preferred ones are those wherein n is 0, 3, or 4; and R is

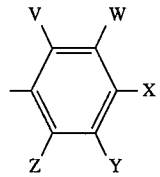

wherein

V and Y are hydrogen; and

W and X are independently selected from hydrogen, halogen (e.g., chlorine), lower alkyl (e.g., n-C$_4$H$_9$), lower alkoxy (e.g., —OCH$_3$), cycloalkylalkyl (e.g., 5-cyclohexylpentyl), arylalkyl (e.g., phenylmethyl, 2-phenylethyl, 5-phenylpentyl), and heteroarylalkyl (e.g., pyridin-4-yl-methyl); with the proviso that when n is 3 or 4, W and X are hydrogen.

Specific preferred compounds are those compounds having pI$_{50}$ values of 4.8 or higher, as determined from results of a diet test conducted against the tobacco budworm. These compounds are Compounds 4, 5, 7, 21, 29, 41, 42, 43, 45, and 47 of Table 1, below; their test results are reported in Table 3.

For the purposes of this invention, as regards the above substituent groups, the following definitions apply:

The term alkyl includes straight or branched chained alkyl of 1 to 14 carbon atoms, preferably lower straight or branched alkyl of 1 to 6 carbon atoms; while halogen includes chlorine, bromine, fluorine and iodine atoms. The term haloalkyl includes straight or branched chain alkyl of 1 to 14 carbon atoms, preferably lower straight or branched alkyl of 1 to 6 carbon atoms, wherein one or more hydrogen atoms have been replaced with halogen atoms, as, for example, trifluoromethyl. The terms alkylthio and alkylsulfinyl include straight or branched chain alkyl of 1 to 14 carbon atoms, preferably lower straight or branched alkyl of 1 to 6 carbon atoms, e.g., methylthio and methylsulfinyl, respectively. The terms lower alkoxy, lower dialkylamino, and lower alkoxycarbonyl include those moieties having 1 to 6 carbon atoms, e.g., ethoxy, N,N-dimethylamino, and methoxycarbonyl, respectively.

The terms aryl and substituted aryl include phenyl and naphthyl, preferably phenyl or substituted phenyl. The term substituted aryl includes those groups substituted with one or more alkyl, halo, haloalkyl, or lower alkoxycarbonyl groups, or the like.

The term aryloxy includes phenoxy, naphthoxy, substituted phenoxy and substituted naphthoxy, preferably phenoxy and substituted phenoxy. The term substituted aryloxy includes those groups substituted with one or more alkyl, halo, haloalkyl, or lower alkoxycarbonyl groups, or the like.

DETAILED DESCRIPTION OF THE INVENTION

Synthesis of The Compounds

The compounds employed as insecticides in accordance with this invention are generally known to those skilled in the art, including commercial preparations thereof, or may readily be prepared from these compounds by known methods. These and other methods are described in further detail in the description, reaction scheme, and examples below.

Thus, in general, these compounds may be prepared by methods, or slight modifications thereof, taught by E. J. Modest and P. Levine [JOC, 21, 14–20 (1956)]. Briefly, an appropriately substituted amine hydrochloride, for example, 3-phenyl-1-propylamine hydrochloride (A) was reacted with cyanoguanidine, affording the corresponding N-[(N'-substituted amino)iminomethyl]guanidine (B). The so-prepared N-[(N-substituted amino)iminomethyl]guanidine was either condensed in-situ, or isolated and then condensed, with an appropriate ketone, for example, acetone under acidic conditions, yielding the targeted triazine hydrochlorides (I), for example, 1-(3-phenylpropyl)-2,4-diamino-6,6-dimethyl-1, 6-dihydro-1,3,5-triazine hydrochloride. The intermediate substituted amine hydrochlorides (A) were also prepared by methods known to one skilled in the art. The following reaction scheme represents one method used to prepare the compounds of the present invention. Examples 1–4 provide detailed descriptions of how these reactions were conducted.

Reaction Scheme

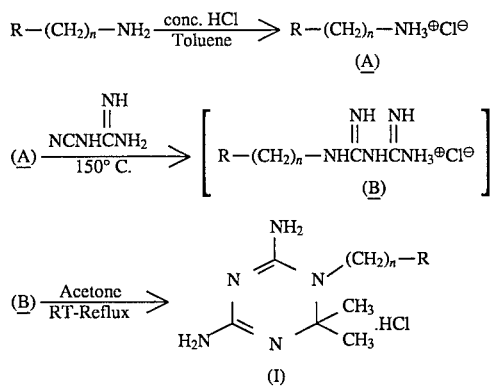

EXAMPLES

The following examples are by way of illustration only, and are not intended to limit the scope of the invention claimed herein.

The products of these examples are summarized in Table 1 below, while their corresponding empirical formulas and characterizing data are listed in Table 2.

Example 1

Synthesis of
1-(3-Phenylpropyl)-2,4-Diamino-6,6-Dimethyl-
1,6-Dihydro-1,3,5-Triazine Hydrochloride
(Compound 4)

Step A Synthesis of N-[(N'-3-phenylpropylamino)iminomethyl]guanidine hydrochloride as an intermediate A solution of 5.0 grams (0.037 mole) of 3-phenyl-1-propylamine in 30 mL of toluene was stirred, and 3.4 mL (0.041 mole) of concentrated hydrochloric acid was added. Upon completion of addition, the reaction mixture was stirred for about 10 minutes. After this time the reaction mixture was concentrated under reduced pressure, and another 30 mL of toluene was added. The reaction mixture was again concentrated under reduced pressure to a residue. The residue was slurried in about 30 mL of diethyl ether, and solid 3-phenyl-1-propylamine hydrochloride was collected by filtration. The 3-phenyl-1-propylamine hydrochloride, 6.0 grams (0.035 mole), was combined with 3.0 grams (0.035 mole) of cyanoguanidine, and the combination was slowly warmed to about 140° C. during a 3.5 hour period. After this time the reaction mixture was cooled, and 40 mL of acetone was added. The resultant solid was collected by filtration and washed with acetone, yielding 4.6 grams of N-[(N'-3-phenylpropylamino)iminomethyl]guanidine hydrochloride, mp 122°–125° C. The NMR spectrum was consistent with the proposed structure.

Step B Synthesis of 1-(3-phenylpropyl)-2,4-diamino-6,6-dimethyl-1,6-dihydro-1,3,5-triazine hydrochloride (Compound 4)

Under a nitrogen atmosphere, a stirred mixture of 4.0 grams (0.016 mole) of N-[(N'-3-phenylpropylamino)iminomethyl]guanidine hydrochloride, 6.2 mL of 2,2-dimethoxypropane, and four drops of concentrated hydrochloric acid in 37 mL of acetone was heated at reflux for about 24 hours. The reaction mixture was then cooled, and a solid was collected by filtration. The solid was washed with acetone and recrystallized from ethanol, yielding 1.0 gram of 1-(3-phenylpropyl)-2,4-diamino-6,6-dimethyl-1,6-dihydro-1,3,5-triazine hydrochloride, mp 227°–230° C. The NMR spectrum was consistent with the proposed structure.

Example 2

Synthesis of
1-(3-Chloro-4-Methoxyphenyl)-2,4-Diamino-
6,6-Dimethyl-1,6-Dihydro-1,3,5-Triazine
Hydrochloride (Compound 29)

A stirred mixture of 3.0 grams (0.019 mole) of 90% pure 3-chloro-4-methoxyaniline and 4 mL of concentrated hydrochloric acid in 20 mL of toluene was heated to reflux using a heat gun. The reaction mixture was then concentrated under reduced pressure to a residue. The residue was triturated with 50 mL of diethyl ether, and the resultant solid was collected by filtration. The solid was dried under vacuum, yielding 3.4 grams (0.018 mole) of 3-chloro-4-methoxyaniline hydrochloride. A stirred mixture of the aniline hydrochloride and 1.8 grams (0.022 mole) of cyanoguanidine in 25 mL of acetone was then heated at reflux for about 20 hours. The mixture was cooled, and a solid was collected by filtration. The solid was dried under vacuum, yielding 4.9 grams of 1-(3-chloro-4-methoxyphenyl)-2,4-diamino-6,6-dimethyl-1,6-dihydro-1,3,5-triazine hydrochloride, mp 232 ° C. The NMR spectrum was consistent with the proposed structure.

Example 3

Synthesis of
1[-3-(5-Cyclohexylpentyl)Phenyl]-2,4-Diamino-
6,6-Dimethyl-1,6-Dihydro-1,3,5-Triazine
Hydrochloride (Compound 41)

Step A Synthesis of 3-(5-cyclohexylpentyn-1-yl)aniline as an intermediate

Under a nitrogen atmosphere, a mixture of 4.4 mL (0.037 mole) of 3-iodoaniline, 6.5 grams (0.043 mole) of 1-cyclohexyl-4-pentyne, 0.3 gram (catalyst) of bis(triphenylphosphine)palladium(II) chloride, 0.7 gram (catalyst) of copper(I) chloride, and 20.4 mL (0.146 mole) of triethylamine in 100 mL of acetonitrile was stirred at ambient temperature for about 18 hours. After this time the reaction mixture was poured into 200 mL of water, and this mixture then was extracted with three 100 mL portion of diethyl ether. The combined extracts were washed with three 100 mL portions of aqueous 10% citric acid solution and then with one 100 mL portion of an aqueous solution saturated with sodium chloride. The organic layer was dried with magnesium sulfate and filtered. The filtrate was concentrated under reduced pressure to a residue. The residue was subjected to column chromatography on silica gel, using 10% methylene chloride in diethyl ether as the eluant. The product-containing fractions were combined and concentrated under reduced pressure, yielding 11.0 grams of 3-( 5-cyclohexylpentyn-1-yl)aniline that was about 91% pure. The NMR spectrum was consistent with the proposed structure.

Step B Synthesis of 3-(5-cyclohexylpentyl)aniline hydrochloride as an intermediate A mixture of 11.0 grams (0.045 mole) of 3-(5-cyclohexylpentyn-1-yl)aniline and 0.3 gram (catalyst) of platinum oxide in 150 mL of ethanol was subjected to hydrogenation using a Parr hydrogenator. Upon completion of four hours of hydrogenation, gas chromatographic (GC) analysis of the reaction mixture indicated that the reaction was not complete. The spent catalyst was filtered from the reaction mixture, and 0.3 gram of fresh platinum oxide was added. The hydrogenation was then continued until it was completed, as determined by GC analysis. The reaction mixture was then concentrated under reduced pressure to a residue. The residue was dissolved in diethyl ether and treated with an excess of an ethereal solution of hydrogen chloride. The resultant solid precipitate was collected by filtration and washed with diethyl ether. The solid was recrystallized from methanol, yielding 3.8 grams of 3-(5-cyclohexylpentyl)aniline hydrochloride, mp 137°–139° C. The NMR spectrum was consistent with the proposed structure.

Step C Synthesis of 1-[3-(5-cyclohexylpentyl)phenyl]-2,4-diamino-6,6-dimethyl-1,6-dihydro-1,3,5-triazine hydrochloride (Compound 41)

Under a nitrogen atmosphere, a solution of 2.8 grams (0.010 mole) of 3-(5-cyclohexylpentyl)aniline hydrochloride and 0.9 gram (0.011 mole) of cyanoguanidine in 100 mL of acetone was stirred at ambient temperature for about four days. After this time, the reaction mixture was filtered to collect a solid. The solid was recrystallized from methanol/diethyl ether and then from water, yielding 2.7 grams of 1-[3-(5-cyclohexylpentyl)phenyl]-2,4-diamino-6,6-dimethyl-1,6-dihydro-1,3,5-triazine hydrochloride, mp 188°–190° C. The NMR spectrum was consistent with the proposed structure.

Example 4

Synthesis of 1-[3-(Naphth-2-Yloxymethyl)Phenyl]-2,4-Diamino-6,6-Dimethyl-1,6-Dihydro-1,3,5-Triazine Hydrochloride (Compound 48)

Step A Synthesis of 3-(naphth-2-yloxymethyl)nitrobenzene as an intermediate

A stirred solution of 3.8 grams (0.026 mole) of 2-naphthol and 3.6 grams (0.026 mole) of potassium carbonate in 200 mL of acetone was heated at reflux for about 30 minutes. The reaction mixture was then cooled to ambient temperature, and 5.0 grams (0.023 mole) of 3-nitrophenylmethyl bromide was added. Upon completion of addition, the reaction mixture was stirred at ambient temperature for 30 minutes. The reaction mixture was then warmed to reflux where it stirred for about 18 hours. After this time the reaction mixture was cooled to ambient temperature and filtered. The filtrate was concentrated under reduced pressure to a residue. The residue was partitioned between ethyl acetate and an aqueous solution saturated with sodium bicarbonate. The organic layer was separated and washed with three 50 mL portions of an aqueous solution saturated with sodium bicarbonate and then with one 50 mL portion of an aqueous solution saturated with sodium chloride. The organic layer was dried with magnesium sulfate, filtered, and the filtrate concentrated under reduced pressure to a residue. The residue was crystallized with hexane, yielding about 4.5 grams of 3-(naphth-2-yloxymethyl)nitrobenzene. The NMR spectrum was consistent with the proposed structure.

Step B Synthesis of 3-(naphth-2-yloxymethyl)aniline hydrochloride as an intermediate Under a nitrogen atmosphere, a stirred mixture of 4.5 grams (0.016 mole) 3-(naphth-2-yloxymethyl)nitrobenzene and 4.5 grams (0.081 mole) of iron powder in 10 mL of water and 50 mL of acetic acid was heated at reflux for about six hours. After this time the reaction mixture was cooled to ambient temperature, and 100 mL of methylene chloride was added. The mixture was filtered, and an additional 100 mL of methylene chloride was added to the filtrate. The methylene chloride layer was separated and washed with four portions of an aqueous solution saturated with sodium bicarbonate and then with two portions of an aqueous solution saturated with sodium chloride. The organic layer was dried with magnesium sulfate, filtered, and the filtrate was concentrated under reduced pressure to a residue. The residue was then dissolved in diethyl ether and treated with an excess of an ethereal solution of hydrogen chloride. The resultant precipitate was collected by filtration and recrystallized from ethyl acetate and diethyl ether, yielding 3.1 grams of 3-(naphth-2-yloxymethyl)aniline hydrochloride. The NMR spectrum was consistent with the proposed structure.

Step C Synthesis of 1-[3-(naphth-2-yloxymethyl )phenyl]-2,4-diamino-6,6-dimethyl-1,6-dihydro-1,3,5-triazine hydrochloride (Compound 48)

This compound was prepared in a manner analogous to that of Step C of Example 3, using 0.42 gram (0.005 mole) of 3-(naphth-2-yloxymethyl)aniline hydrochloride and 0.33 gram (0.005 mole) of cyanoguanidine in 100 mL of acetone. The solid product was recrystallized from water, yielding 1.54 grams of 1-[3-(naphth-2-yloxymethyl)phenyl]-2,4-diamino-6,6-dimethyl-1,6-dihydro-1,3,5-triazine hydrochloride, mp 172°–174° C. The NMR spectrum was consistent with the proposed structure.

TABLE 1

1-Substituted-2,4-diamino-6,6-dialkyl-1,6-dihydro-1,3,5-triazines as Insecticides $$\text{structure with } (CH_2)_n\text{-R, where R is substituted phenyl with V, W, X, Y, Z}$$

| Cmpd. No. | n | V | W | X | Y | Z | R |
|---|---|---|---|---|---|---|---|
| 1 | 0 | H | H | H | H | H | HCl salt |
| 2 | 1 | H | H | H | H | H | HCl salt |
| 3 | 2 | H | H | H | H | H | HCl salt |
| 4 | 3 | H | H | H | H | H | HCl salt |
| 5 | 4 | H | H | H | H | H | HCl salt |
| 6 | 0 | Cl | H | H | H | H | HCl salt |
| 7 | 0 | H | Cl | H | H | H | HCl salt |
| 8 | 0 | H | H | Cl | H | H | HCl salt |
| 9 | 0 | H | H | F | H | H | HCl salt |
| 10 | 0 | Cl | Cl | H | H | H | HCl salt |
| 11 | 0 | Cl | H | Cl | H | H | HCl salt |
| 12 | 0 | H | Cl | Cl | H | H | |
| 13 | 0 | H | Cl | Cl | H | H | HCl salt |
| 14 | 0 | H | F | F | H | H | HCl salt |
| 15 | 0 | H | Cl | H | Cl | H | HCl salt |
| 16 | 0 | Cl | Cl | Cl | H | H | HCl salt |
| 17 | 0 | Cl | H | Cl | Cl | H | HCl salt |
| 18 | 0 | H | Cl | Cl | Cl | H | HCl salt |
| 19 | 0 | H | H | n-C$_3$H$_7$ | H | H | HCl salt |
| 20 | 0 | H | —CH(CH$_3$)$_2$ | H | H | H | HCl salt |
| 21 | 0 | H | n-C$_4$H$_9$ | H | H | H | HCl salt |
| 22 | 0 | H | —CH(CH$_3$)(C$_2$H$_5$) | H | H | H | HCl salt |
| 23 | 0 | H | —C$_2$H$_5$ | —C$_2$H$_5$ | H | H | HCl salt |
| 24 | 0 | H | —CH$_3$ | —CH$_3$ | —CH$_3$ | H | |
| 25 | 0 | H | Cl | —CH(CH$_3$)$_2$ | H | H | HCl salt |
| 26 | 0 | H | —CH(CH$_3$)$_2$ | Cl | H | H | HCl salt |
| 27 | 0 | H | —CF$_3$ | H | H | H | HCl salt |
| 28 | 0 | H | H | —OCH$_3$ | H | H | HCl salt |
| 29 | 0 | H | Cl | —OCH$_3$ | H | H | HCl salt |
| 30 | 0 | H | n-OC$_4$H$_9$ | H | H | H | HCl salt |
| 31 | 0 | H | n-OC$_5$H$_{11}$ | H | H | H | HCl salt |
| 32 | 0 | H | n-OC$_5$H$_{11}$ | H | Cl | H | HCl salt |
| 33 | 0 | H | Cl | n-OC$_5$H$_{11}$ | H | H | HCl salt |
| 34 | 0 | H | H | —SCH$_3$ | H | H | |

TABLE 1-continued

1-Substituted-2,4-diamino-6,6-dialkyl-1,6-dihydro-1,3,5-triazines as Insecticides

| Cmpd. No. | n | V | W | X | Y | Z | R |
|---|---|---|---|---|---|---|---|
| 35 | 0 | H | —SCH$_3$ | —SCH$_3$ | H | H HCl salt | |
| 36 | 0 | H | —CN | H | H | H HCl salt | |
| 37 | 0 | H | —NO$_2$ | H | H | H HCl salt | |
| 38 | 0 | H | —N(CH$_3$)$_2$ | H | H | H 2HCl salt | |
| 39 | 0 | H | Cl | —N(CH$_3$)$_2$ | H | H 2HCl salt | |
| 40 | 0 | H | —CH$_2$N(C$_2$H$_5$)$_2$ | H | H | H 2HCl salt | |
| 41 | 0 | H | \-—C$_5$H$_{10}$—(cyclohexyl) | H | H | H HCl salt | |
| 42 | 0 | H | \-—CH$_2$—(phenyl) | H | H | H HCl salt | |
| 43 | 0 | H | \-—C$_2$H$_4$—(phenyl) | H | H | H HCl salt | |
| 44 | 0 | H | \-—CH(CH$_3$)—(phenyl) | H | H | H HCl salt | |
| 45 | 0 | H | \-—C$_5$H$_{10}$—(phenyl) | H | H | H HCl salt | |
| 46 | 0 | H | Cl | \-—C$_4$H$_8$—(phenyl with SO$_2$F and Cl) | H | H | |
| 47 | 0 | H | H | \-—CH$_2$—(pyridyl) | H | H 2HCl salt | |
| 48 | 0 | H | \-—OC$_2$H$_4$—(naphthyl) | H | H | H HCl salt | |
| 49 | 0 | H | H | \-—C(O)CH$_3$ | H | H HCl salt | |

TABLE 1-continued

1-Substituted-2,4-diamino-6,6-dialkyl-1,6-dihydro-1,3,5-triazines as Insecticides

| Cmpd. No. | n | V | W | X | Y | Z | R |
|---|---|---|---|---|---|---|---|
| 50 | 0 | H | H | -CH₂-C(=O)-OC₂H₅ | H | H | HCl salt |
| 51 | 0 | H | -C(=O)-C₆H₅ | H | H | H | HCl salt |
| 52 | 0 | H | -C(=O)-C₆H₅ | H | Cl | H | HCl salt |
| 53 | 0 | H | Cl | -C(=O)-C₆H₅ | H | H | HCl salt |
| 54 | 0 | H | H | -C(=O)-CH₂CH₂CH₂-NH-C₆H₄-SO₂H (para) | H | H | HCl salt |
| 55 | 0 | H | H | -CH₂-O-CH₂-C₆H₅ | H | H | HCl salt |
| 56 | 0 | H | H | -CH₂-O-CH₂-C₆H₄-Cl (ortho) | H | H | HCl salt |
| 57 | 0 | H | H | -CH₂-O-CH₂-C₆H₄-Cl (meta) | H | H | HCl salt |
| 58 | 0 | H | H | -CH₂-O-CH₂-C₆H₄-Cl (para) | H | H | HCl salt |
| 59 | 0 | H | Cl | -CH₂-O-CH₂-C₆H₅ | H | H | HCl salt |
| 60 | 0 | H | Cl | -CH₂-O-CH₂-C₆H₄-Cl (ortho) | H | H | HCl salt |

TABLE 1-continued

1-Substituted-2,4-diamino-6,6-dialkyl-1,6-dihydro-1,3,5-triazines as Insecticides $$\text{structure with } NH_2, N, (CH_2)_n-R, CH_3, CH_3 \text{ groups}$$

where R is a phenyl ring with substituents V, W, X, Y, Z

| Cmpd. No. | n | V | W | X | Y | Z | R |
|---|---|---|---|---|---|---|---|
| 61 | 0 | H | Cl | -O-CH₂-(3-chlorophenyl) | | H | H HCl salt |
| 62 | 0 | H | Cl | -O-CH₂-(4-chlorophenyl) | | H | H HCl salt |
| 63 | 0 | H | | -O-CH₂-(decahydronaphthyl) | H | H | H HCl salt |
| 64 | 0 | | —OC(CH₃)₂CH₂— | H | | H | H HCl salt |
| 65 | 2 | | | | | | —CH(CH₃)₂ |

TABLE 2

EMPIRICAL FORMULA AND CHARACTERIZING DATA

| Cmpd No | Empirical Formula | MP (°C.)/Physical State |
|---|---|---|
| 1 | $C_{11}H_{15}N_5.HCl$ | 222–224 |
| 2 | $C_{12}H_{17}N_5.HCl$ | 208–210 |
| 3 | $C_{13}H_{19}N_5.HCl$ | 221–223 |
| 4 | $C_{14}H_{21}N_5.HCl$ | 227–230 |
| 5 | $C_{15}H_{23}N_5.HCl$ | 216–218 |
| 6 | $C_{11}H_{14}ClN_5.HCl$ | 223–226 |
| 7 | $C_{11}H_{14}ClN_5.HCl$ | 210–211 |
| 8 | $C_{11}H_{14}ClN_5.HCl$ | 226–227 |
| 9 | $C_{11}H_{14}FN_5.HCl$ | SOLID |
| 10 | $C_{11}H_{13}Cl_2N_5.HCl$ | 214–216 |
| 11 | $C_{11}H_{13}Cl_2N_5.HCl$ | 222–224 |
| 12 | $C_{11}H_{13}Cl_2N_5$ | SOLID |
| 13 | $C_{11}H_{13}Cl_2N_5.HCl$ | 220–222 |
| 14 | $C_{11}H_{13}F_2N_5.HCl$ | SOLID |
| 15 | $C_{11}H_{13}Cl_2N_5.HCl$ | 226–230 |
| 16 | $C_{11}H_{12}Cl_3N_5.HCl$ | 224–226 |
| 17 | $C_{11}H_{12}Cl_3N_5.HCl$ | SOLID |
| 18 | $C_{11}H_{12}Cl_3N_5.HCl$ | 247–248 |
| 19 | $C_{14}H_{21}N_5.HCl$ | 222–223 |
| 20 | $C_{14}H_{21}N_5.HCl$ | 220–221 |
| 21 | $C_{15}H_{23}N_5.HCl$ | 178–180 |
| 22 | $C_{15}H_{23}N_5.HCl$ | 198–199 |
| 23 | $C_{15}H_{23}N_5.HCl$ | 218–219 |
| 24 | $C_{14}H_{21}N_5$ | SOLID |
| 25 | $C_{14}H_{20}ClN_5.HCl$ | 220–222 |
| 26 | $C_{14}H_{20}ClN_5.HCl$ | 227 |
| 27 | $C_{12}H_{14}F_3N_5.HCl$ | SOLID |
| 28 | $C_{12}H_{17}N_5O.HCl$ | 232 |
| 29 | $C_{12}H_{16}ClN_5O.HCl$ | 232 |
| 30 | $C_{15}H_{23}N_5O.HCl$ | 190–191 |
| 31 | $C_{16}H_{25}N_5O.HCl$ | 200–201 |
| 32 | $C_{16}H_{24}ClN_5O.HCl$ | 179–180 |
| 33 | $C_{16}H_{24}ClN_5O.HCl$ | 213–215 |
| 34 | $C_{12}H_{17}N_5S_2.HCl$ | SOLID |
| 35 | $C_{13}H_{19}N_5S_2.HCl$ | SOLID |
| 36 | $C_{12}H_{14}N_6.HCl$ | 217–219 |
| 37 | $C_{11}H_{14}N_6O_2.HCl$ | SOLID |
| 38 | $C_{13}H_{20}N_6.2HCl$ | 224–226 |
| 39 | $C_{13}H_{19}ClN_6.2HCl$ | 223–225 |
| 40 | $C_{16}H_{26}N_6.2HCl$ | 187–191 |
| 41 | $C_{22}H_{35}N_5.HCl$ | 188–190 |
| 42 | $C_{18}H_{21}N_5.HCl$ | 186–190 |
| 43 | $C_{19}H_{23}N_5.HCl$ | 205–207 |
| 44 | $C_{20}H_{25}N_5.HCl$ | 186–188 |
| 45 | $C_{22}H_{29}N_5.HCl$ | 174–176 |
| 46 | $C_{21}H_{24}Cl_2FN_5O_2S$ | SOLID |
| 47 | $C_{17}H_{20}N_6.2HCl$ | 217–219 |
| 48 | $C_{22}H_{23}N_5O.HCl$ | 172–174 |
| 49 | $C_{13}H_{17}N_5O.HCl$ | SOLID |
| 50 | $C_{14}H_{19}N_5O_2$ | 246–247 |
| 51 | $C_{18}H_{19}N_5O.HCl$ | 235–237 |
| 52 | $C_{18}H_{18}ClN_5O.HCl$ | 213–215 |
| 53 | $C_{18}H_{18}ClN_5O.HCl$ | 224–225 |
| 54 | $C_{20}H_{23}FN_6O_3S.HCl$ | 235–238 |
| 55 | $C_{18}H_{21}N_5O.HCl$ | 230–232 |
| 56 | $C_{18}H_{20}ClN_5O.HCl$ | 214–215 |
| 57 | $C_{18}H_{20}ClN_5O.HCl$ | 215–216 |
| 58 | $C_{18}H_{20}ClN_5O.HCl$ | 234–235 |
| 59 | $C_{18}H_{20}ClN_5O.HCl$ | 216–217 |
| 60 | $C_{18}H_{19}Cl_2N_5O.HCl$ | 217–218 |
| 61 | $C_{18}H_{19}Cl_2N_5O.HCl$ | 213–214 |
| 62 | $C_{18}H_{19}Cl_2N_5O.HCl$ | 215–216 |
| 63 | $C_{21}H_{31}N_5O.HCl$ | 198–199 |
| 64 | $C_{15}H_{21}N_5O.HCl$ | 244–247 |
| 65 | $C_{10}H_{21}N_5.HCl$ | 220–222 |

Insecticide Formulations

In the normal use of the insecticidal substituted triazines of the present invention, they usually will not be employed free from admixture or dilution, but ordinarily will be used in a suitable formulated composition compatible with the method of application and comprising an insecticidally effective amount of the triazine. The triazines of this invention, like most pesticidal agents, may be blended with the agriculturally acceptable surface-active agents and carriers normally employed for facilitating the dispersion of active ingredients, recognizing the accepted fact that the formulation and mode of application of an insecticide may affect the activity of the material. The present substituted triazines may be applied, for example, as sprays, dusts, or granules to the area where pest control is desired, the type of application varying of course with the pest and the environment. Thus, the triazines of this invention may be formulated as granules of large particle size, as powdery dusts, as wettable powders, as emulsifiable concentrates, as solutions, and the like. It will be understood that the insecticides themselves may be present as essentially pure compounds, or as mixtures of these triazine compounds.

Granules may comprise porous or nonporous particles, such as attapulgite clay or sand, for example, which serve as carriers for the triazines. The granule particles are relatively large, a diameter of about 400–2500 microns typically. The particles are either impregnated with the triazine from solution or coated with the triazine, adhesive sometimes being employed. Granules generally contain 0.05–10%, preferably 0.5–5%, active ingredient as the insecticidally effective amount.

Dusts are admixtures of the triazines with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the insecticide. These finely divided solids have an average particle size of less than about 50 microns. A typical dust formulation useful for controlling insects contains 1 part of Compound 13 and 99 parts of talc.

The triazines of the present invention may be made into liquid concentrates by dissolution or emulsification in suitable liquids and into solid concentrates by admixture with talc, clays, and other known solid carriers used in the pesticide art. The concentrates are compositions containing, as an insecticidally effective amount, about 5–50% triazine, and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts.

By way of illustration, compound 13 is formulated as a 10% wettable powder (10% WP) as follows:

| COMPONENT | AMOUNT (wt/wt) |
|---|---|
| Compound 13 | 10.1% |
| Wetting Agent | 5.0% |
| Dispersing Agent | 3.8% |
| Wetting/Dispersing Agent | 0.9% |
| Diluent | 80.2% |

Manufacturing concentrates are useful for shipping low melting products of this invention. Such concentrates are prepared by melting the low melting solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the triazines with a liquid or solid emulsifying agent, or they may also contain a liquid carrier such as xylene, heavy aromatic naphthas, isophorone and other relatively nonvolatile organic solvents. For application, these concentrates are dispersed in water or other liquid carriers and normally applied as sprays to areas to be treated.

Typical surface-active wetting, dispersing, and emulsifying agents used in pesticidal formulations include, for example, the alkyl and alkylaryl sulfonates and sulfates and their sodium salts, including fatty methyl taurides; alkylaryl polyether alcohols; sulfates of higher alcohols; polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the insecticidal composition.

Other useful formulations include simple solutions of the active ingredient in a solvent in which it is completely soluble at the desired concentrations, such as acetone or other organic solvents.

As shown in the biological test methods below, the compounds of the present invention were tested in the laboratory as dimethyl sulfoxide solutions incorporated into an artificial insect diet or as aqueous acetone or methanol solutions containing a small amount of octylphenoxypolyethoxyethanol surfactant for use as foliar sprays. An insecticidally effective amount of substituted triazine in an insecticidal composition diluted for application is normally in the range of about 0.001% to about 8% by weight. Many variations of spraying and dusting compositions known in the art may be used by substituting the triazine of this invention into compositions known or apparent in the art.

The insecticidal compositions of this invention may be formulated with other active ingredients, including other insecticides, nematicides, acaricides, fungicides, plant growth regulators, fertilizers, etc.

In using the compositions to control insects, it is only necessary that an insecticidally effective amount of triazine be applied to the locus where control is desired. Such locus may, e.g., be the insects themselves, plants upon which the insects feed, or the insect habitat. When the locus is the soil, e.g., soil in which agricultural crops are or will be planted, the active compound may be applied to and optionally incorporated into the soil. For most applications, an insecticidally effective amount will be about 75 to 4000 g per hectare, preferably 150 g to 3000 g per hectare.

Biological Data

The substituted triazines of the present invention were incorporated into an artificial diet for evaluation of insecticidal activity against the tobacco budworm (*Heliothis virescens* [Fabricius]).

Stock solutions of test chemical in dimethyl sulfoxide were prepared for each rate of application. The rates of application, expressed as the negative log of the molar concentration, and the corresponding concentrations of the stock solution prepared for each rate are shown below:

| Stock Solution | Rate of Application |
|---|---|
| 50 micromolar | 4 |
| 5 | 5 |
| 0.5 | 6 |
| 0.05 | 7 |
| 0.005 | 8 |

One hundred microliters of each of the stock solutions was manually stirred into 50 mL of a molten (65°–70° C.)

wheat germ-based artificial diet. The 50 mL of molten diet containing the test chemical was poured evenly into twenty wells in the outer four rows of a twenty-five well, five row plastic tray. Each well in the tray was about 1 cm in depth, with an opening of 3 cm by 4 cm at the lip. Molten diet containing only dimethyl sulfoxide at the levels used in the test chemical-treated diet was poured into the five wells in the third row of the tray. Each tray therefore contained one test chemical at a single rate of application, together with an untreated control. Single second instar tobacco budworm larvae were placed in each well. The larvae were selected at a stage of growth at which they uniformly weigh about 5 mg each. Upon completion of infestation, a sheet of clear plastic was heat-sealed over the top of the tray using a common household flat iron. The trays were held at 25 ° C. at 60% relative humidity for five days in a growth chamber. Lighting was set at 14 hours of light and 10 hours of darkness.

After the 5-day exposure period, mortality counts were taken, and the surviving insects were weighed. From the weights of the surviving insects that fed on the treated diet as compared to those insects that fed on the untreated diet, the percent growth inhibition caused by each test chemical was determined. From these data, the negative log of the concentration of the test chemical that provided 50% growth inhibition ($pI_{50}$) was determined by linear regression, when possible, for each test chemical. The results are reported in Table 3, below, from which it will be seen that most were effective in inhibiting the growth of the tobacco budworm.

Certain substituted-2,4-diaminoquinazoline derivatives with high $pI_{50}$ values from the diet test were also tested for insecticidal activity in foliar evaluations against the tobacco budworm, beet armyworm (*Spodoptera exigua* [Hubner]), and the cabbage looper (*Trichoplusia ni* [Hubner]). The results of these tests are shown in Table 4, below.

In these tests against the tobacco budworm and the beet armyworm, nine-day-old chick pea plants (*Cicer arietinum*) were sprayed at 20 psi to runoff on both upper and lower leaf surfaces with solutions of test chemical to provide application rates as high as 1000 ppm of test chemical. The solvent used to prepare the solutions of test chemical was 10% acetone or methanol (v/v) and 0.1% of the surfactant octylphenoxypolyethoxyethanol in distilled water. Four replicates, each containing four chick pea plants, for each rate of application of test chemical were sprayed. The treated plants were transferred to a hood where they were kept until the spray had dried.

The four chick pea plants in each replicate treated with test chemical as described above were removed from their pots by cutting the stems just above the soil line. The excised leaves and stems from the four plants in each replicate were placed in individual 8-ounce paper cups, which contained a moistened filter paper. Five second-instar (4–5 days old) tobacco budworms or beet armyworms were counted into each cup, taking care not to cause injury. An opaque plastic lid was placed on each cup, which was then held in a growth chamber for a 96 hour exposure period at 25° C. and 50% relative humidity. At the end of the 96 hour exposure period the cups were opened, and the numbers of dead and live insects were counted. Moribund larvae which were disoriented or unable to crawl normally were counted as dead. Using the insect counts, the efficacy, i.e., the percent control, of the test chemical was observed for phytotoxicity and for reduction of feeding damage as compared to an untreated control.

Foliar tests with cabbage looper were conducted in the same manner as described above, the difference being that pinto bean plants (*Phaseolus vulgaris*) were used.

TABLE 3

Insecticidal Activity of 1-Substituted-2,4-diamino-6,6-dialkyl-1,6-dihydro-1,3,5-triazines Incorporated into the Diet of Tobacco Budworm

| Cmpd. No. | Rate of Application[1] | Percent Growth Inhibition[2,3] | $pI_{50}$[4] |
|---|---|---|---|
| 1 | 6 | −18 | 4.1 |
|   | 5 | 25 |   |
|   | 4 | 50 |   |
| 2 | 4 | 7 | — |
| 3 | 5 | −17 | — |
|   | 4 | 14 |   |
| 4 | 6 | 14 | 5.2 |
|   | 5 | 74 |   |
|   | 4 | 93 |   |
|   | 6 | 40 | 5.7 |
|   | 5 | 71 |   |
|   | 4 | 90 |   |
| 5 | 6 | 2 | 4.9 |
|   | 5 | 49 |   |
|   | 4 | 87 |   |
|   | 6 | 2 | 4.8 |
|   | 5 | 48 |   |
|   | 4 | 75 |   |
| 7 | 6 | 5 | 4.8 |
|   | 5 | 29 |   |
|   | 4 | 86 |   |
|   | 6 | 9 | 4.8 |
|   | 5 | 38 |   |
|   | 4 | 85 |   |
| 9 | 5 | −13 | <4.0 |
|   | 4 | 23 |   |
| 17 | 4 | −3 | — |
| 20 | 5 | 37 | 4.6 |
|   | 4 | 66 |   |
| 21 | 6 | −10 | 4.9 |
|   | 5 | 52 |   |
|   | 4 | 86 |   |
| 22 | 5 | 12 | 4.4 |
|   | 4 | 74 |   |
| 27 | 5 | −16 | 4.2 |
|   | 4 | 70 |   |
| 28 | 5 | 31 | <4.0 |
|   | 4 | 38 |   |
| 29 | 6 | 29 | 5.5 |
|   | 5 | 77 |   |
|   | 4 | 91 |   |
| 30 | 4 | 4 | — |
| 31 | 5 | 15 | 4.3 |
|   | 4 | 68 |   |
| 36 | 5 | 60 | — |
|   | 4 | 78 |   |
|   | 6 | −2 | 4.6 |
|   | 5 | 26 |   |
|   | 4 | 80 |   |
| 37 | 5 | −6 | 4.1 |
|   | 4 | 56 |   |
| 38 | 4 | 4 | — |
| 39 | 5 | 28 | 4.6 |
|   | 4 | 79 |   |
| 40 | 4 | −19 | — |
| 41 | 6 | 13 | 5.1 |
|   | 5 | 54 |   |
|   | 4 | 93 |   |
| 42 | 6 | 60 | — |
|   | 5 | 69 |   |
|   | 4 | 90 |   |
|   | 7 | 4 | 5.1 |
|   | 6 | 8 |   |
|   | 5 | 60 |   |
|   | 4 | 89 |   |
| 43 | 6 | 11 | 5.0 |
|   | 5 | 52 |   |
|   | 4 | 86 |   |
| 44 | 6 | 6 | 4.0 |
|   | 5 | 4 |   |

TABLE 3-continued

Insecticidal Activity of 1-Substituted-2,4-diamino-6,6-dialkyl-1,6-dihydro-1,3,5-triazines Incorporated into the Diet of Tobacco Budworm

| Cmpd. No. | Rate of Application[1] | Percent Growth Inhibition[2,3] | pI$_{50}$[4] |
|---|---|---|---|
| | 4 | 51 | |
| 45 | 6 | 12 | 5.1 |
| | 5 | 64 | |
| | 4 | 90 | |
| 46 | 6 | 10 | 4.6 |
| | 5 | 25 | |
| | 4 | 73 | |
| 47 | 6 | 21 | 4.9 |
| | 5 | 51 | |
| | 4 | 73 | |
| 48 | 6 | −4 | 4.7 |
| | 5 | 33 | |
| | 4 | 85 | |
| 51 | 5 | 12 | |
| | 4 | −6 | |
| 53 | 5 | 8 | — |
| | 4 | 18 | |
| 54 | 5 | −26 | — |
| | 4 | −4 | |
| 63 | 5 | −4 | — |
| | 4 | 19 | |
| 64 | 4 | −2 | — |
| 65 | 6 | 2 | 4.7 |
| | 5 | 32 | |
| | 4 | 84 | |

FOOTNOTES
[1]The rate of application is expressed as the negative log of the molar concentration of the test compound in the diet.
[2]Percent growth inhibition is derived from the total weight of the insects (IW) at each rate of application in the test relative to the total weight of insects in an untreated control, % Gr. Inh. = [IW (control)-IW (test)/IW (control)] × 100
[3]A minus % growth inhibition indicates that the insects weighed more at the termination of the test than those in the untreated control.
[4]pI50 is the negative log of the concentration of the test chemical that provides 50% growth inhibition in the test insects.

TABLE 4

Insecticidal Activity of 1-Substituted-2,4-diamino-6,6-dialkyl-1,6-dihydro-1,3,5-triazines Applied as Foliar Sprays

| Cmpd No. | Rate of Application (ppm) | Percent Control[1],[2] | | |
|---|---|---|---|---|
| | | TBW | CL | BAW |
| 2 | 1000 | 0 | | |
| | 300 | 0 | | |
| | 100 | 0 | | |
| 3 | 1000 | 10 | | |
| | 300 | 0 | | |
| | 100 | 0 | | |
| 7 | 3000 | 89 | | |
| | 1000 | 95 | | |
| | 300 | 79 | | |
| | 100 | 56 | | |
| | 30 | 21 | | |
| 13 | 30 | 10 | | |
| | 10 | 5 | | |
| | 3 | 10 | | |
| | 1 | 10 | | |
| | 0.3 | 10 | | |
| 20 | 1000 | 20 | | |
| | 300 | 0 | | |
| | 100 | 0 | | |
| 21 | 3000 | 95 | 5 | |
| | 1000 | 80 | 0 | |
| | 300 | 15 | 0 | |
| | 100 | 5 | 0 | |
| | 30 | 0 | 0 | |
| | 3000 | | 85 | |
| | 1000 | | 15 | |
| | 300 | | 17 | |
| | 100 | | 15 | |
| | 30 | | 5 | |
| 22 | 3000 | 16 | | 10 |
| | 1000 | 0 | | 0 |
| | 300 | 5 | | 0 |
| | 100 | 5 | | 0 |
| | 30 | 5 | | 0 |
| | 3000 | | 11 | |
| | 1000 | | 6 | |
| | 300 | | 5 | |
| | 100 | | 11 | |
| | 30 | | 5 | |
| | 3000 | | 70 | |
| | 1000 | | 16 | |
| | 300 | | 0 | |
| | 100 | | 5 | |
| | 30 | | 11 | |
| 23 | 1000 | 100 | | |
| | 300 | 10 | | |
| | 100 | 10 | | |
| 25 | 1000 | 100 | | |
| | 300 | 50 | | |
| | 100 | 0 | | |
| 26 | 1000 | | | 0 |
| | 300 | 0 | | 0 |
| | 100 | 0 | | 0 |
| | 30 | 0 | | 0 |
| | 10 | | | 0 |
| 28 | 3000 | 17 | | |
| | 1000 | 0 | | |
| | 300 | 0 | | |
| | 100 | 6 | | |
| | 30 | 0 | | |
| 29 | 3000 | 100 | | |
| | 1000 | 100 | | |
| | 300 | 79 | | |
| | 100 | 32 | | |
| | 30 | 16 | | |
| 30 | 3000 | 0 | 20 | 0 |
| | 1000 | 0 | 5 | 0 |
| | 300 | 0 | 11 | 0 |
| | 100 | 0 | 11 | 0 |
| | 30 | 0 | 10 | 0 |
| 31 | 1000 | 0 | | |
| | 300 | 0 | | |
| | 100 | 0 | | |
| 32 | 1000 | 22 | | |
| | 300 | 0 | | |
| | 30 | 0 | | |
| | 10 | 0 | | |
| | 3 | 0 | | |
| 33 | 300 | 35 | | |
| | 100 | 5 | | |
| | 30 | 0 | | |
| 38 | 1000 | 10 | | |
| | 300 | 0 | | |
| | 100 | 0 | | |
| 39 | 1000 | 90 | | |
| | 300 | 32 | | |
| | 100 | 5 | | |
| 41 | 3000 | 100 | 95 | 100 |
| | 1000 | 90 | 95 | 100 |
| | 300 | 89 | 90 | 80 |
| | 100 | 42 | 47 | 37 |
| | 30 | 0 | 5 | 26 |
| 42 | 1000 | 67 | | |
| | 300 | 14 | | |
| | 100 | 0 | | |
| 44 | 3000 | 0 | 30 | 0 |

TABLE 4-continued

Insecticidal Activity of 1-Substituted-2,4-diamino-6,6-dialkyl-1,6-dihydro-1,3,5-triazines Applied as Foliar Sprays

| Cmpd No. | Rate of Application (ppm) | Percent Control[1],[2] TBW | CL | BAW |
|---|---|---|---|---|
|  | 1000 | 0 | 35 | 0 |
|  | 300 | 0 | 16 | 0 |
|  | 100 | 0 | 20 | 0 |
|  | 30 | 0 | 10 | 0 |
| 48 | 3000 | 22 | 95 | 0 |
|  | 1000 | 15 | 65 | 0 |
|  | 300 | 5 | 10 | 0 |
|  | 100 | 5 | 10 | 50 |
|  | 30 | 5 | 5 | 10 |
| 51 | 300 | 0 |  |  |
|  | 30 | 0 |  |  |
|  | 10 | 0 |  |  |
|  | 3 | 0 |  |  |
| 52 | 1000 | 0 |  |  |
|  | 300 | 0 |  |  |
|  | 30 | 0 |  |  |
|  | 10 | 0 |  |  |
|  | 3 | 0 |  |  |
| 53 | 1000 | 0 |  |  |
|  | 300 | 5 |  |  |
|  | 100 | 0 |  |  |
| 54 | 1000 | 0 |  |  |
|  | 300 | 0 |  |  |
|  | 100 | 0 |  |  |
| 55 | 1000 | 20 |  |  |
|  | 300 | 0 |  |  |
|  | 100 | 0 |  |  |
| 56 | 1000 | 43 |  |  |
|  | 300 | 0 |  |  |
|  | 100 | 0 |  |  |
| 57 | 1000 | 6 |  |  |
|  | 300 | 0 |  |  |
|  | 100 | 0 |  |  |
| 58 | 1000 | 50 |  |  |
|  | 300 | 0 |  |  |
|  | 100 | 0 |  |  |
| 59 | 1000 | 100 |  |  |
|  | 300 | 100 |  |  |
|  | 100 | 29 |  |  |
| 60 | 1000 | 100 |  |  |
|  | 300 | 80 |  |  |
|  | 100 | 33 |  |  |
| 61 | 1000 | 95 |  |  |
|  | 300 | 40 |  |  |
|  | 100 | 0 |  |  |
| 62 | 1000 | 100 |  |  |
|  | 300 | 70 |  |  |
|  | 100 | 0 |  |  |

FOOTNOTES
[1]TBW - tobacco budworm
   CL - cabbage looper
   BAW - beet armyworm
[2]Percent control is derived from the total number of dead insects (TD) plus the total number of moribund insects (TM) as compared to the total number of insects (TI) in the test:
$$\% \text{ Control} = \frac{TD + TM}{TI} \times 100$$

We claim:

1. A method for controlling insects which comprises applying to the insect or infested locus thereof where control is desired an insecticidally effective amount of a composition comprising, in admixture with an agriculturally acceptable carrier, a 1,3,5-triazine compound of the formula

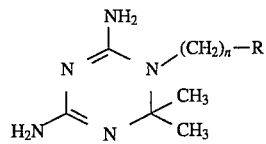

(I)

where n is 0–4; and R is lower alkyl, or

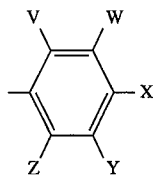

wherein

Z is hydrogen;

V, W, X, and Y are independently selected from hydrogen, halogen, straight or branched chain lower alkyl, lower haloalkyl, lower alkoxy, lower alkylthio, dialkylamino, dialkylaminoalkyl, cyano, nitro, cycloalkylalkyl, bicycloalkoxy, optionally substituted arylalkyl, optionally substituted arylalkoxy, aryloxyalkyl, lower alkylcarbonyl, lower alkoxycarbonyl, arylcarbonyl, and substituted arylaminocarbonylalkyl;

wherein alkyl groups contain from 1 to about 14 carbon atoms; lower alkyl groups contain from 1 to about 6 carbon atoms; cycloalkyl groups contain from about 6 to 10 carbon atoms; aryl comprises carbocyclic aryl of from about 6 to 10 carbon atoms; and the substituents of substituted aryl and aryloxy are selected from one or more of alkyl, halo, haloalkyl, lower alkoxycarbonyl, and halosulfonyl; and agriculturally acceptable salts thereof.

2. The method of claim 1 wherein n is 0, 3, or 4; and R is

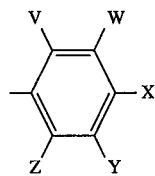

wherein

V and Y are hydrogen; and

W and X are independently selected from hydrogen, halogen, lower alkyl, lower alkoxy, cycloalkylalkyl, and arylalkyl;

with the proviso that when n is 3 or 4, W and X are hydrogen.

3. The method of claim 1 wherein the 1,3,5-triazine is 1-(3-phenylpropyl)-2,4-diamino-6,6-dimethyl-1,6-dihydro-1,3,5-triazine.

4. The method of claim 1 wherein the 1,3,5-triazine is 1-(3-chloro-4-methoxyphenyl)-2,4-diamino-6,6-dimethyl-1,6-dihydro-1,3,5-triazine.

5. The method of claim 1 wherein the triazine is 1-(3,4-dichlorophenyl)-2,4-diamino-6,6-dimethyl-1,6-dihydro-1,3,5-triazine.

6. The method of claim 1 wherein the 1,3,5-triazine is 1-[-3-(5-cyclohexylpentylphenyl]-2,4-diamino-6,6-dimethyl-1,6-dihydro-1,3,5-triazine.

7. The method of claim 1 wherein the surface-active agent is a dispersing, wetting, or emulsifying agent, or mixtures thereof.

* * * * *